United States Patent [19]

Bundy

[11] 4,259,250

[45] Mar. 31, 1981

[54] 11A-HOMO-PG INTERMEDIATES FOR PREPARING 11A-METHANO TXA$_2$ COMPOUNDS

[75] Inventor: Gordon L. Bundy, Portage, Mich.

[73] Assignee: The Upjohn Company, Kalamazoo, Mich.

[21] Appl. No.: 116,077

[22] Filed: Jan. 28, 1980

Related U.S. Application Data

[62] Division of Ser. No. 035,143, May 1, 1979, Pat. No. 4,218,378.

[51] Int. Cl.$^3$ .......................... C09F 7/00; C11C 3/00; C09F 5/08; C11C 1/00

[52] U.S. Cl. ..................................... 260/408; 260/410; 260/410.5; 260/410.9 R; 260/413; 560/60; 560/61; 560/62; 560/51; 560/53; 560/126; 562/459; 562/463; 562/507; 562/508; 568/308; 568/329; 568/377

[58] Field of Search ............... 260/586 R, 590 C, 592, 260/408, 410.5, 410 P, 413 P, 410.9 P, ; 560/60, 61, 62, 51, 53, 126; 562/459, 463, 507, 508; 568/308, 329, 377

[56] References Cited

U.S. PATENT DOCUMENTS

| | | | |
|---|---|---|---|
| 3,993,674 | 11/1976 | Schaub et al. | 260/410.9 P |
| 4,058,564 | 11/1977 | Smith | 260/586 R |

*Primary Examiner*—John F. Niebling
*Attorney, Agent, or Firm*—Robert A. Armitage

[57] ABSTRACT

The present invention provides novel thromboxane analogs and intermediates. Particularly, the present invention provides novel 11a-homo-PG intermediates for preparing 11a-methano TXA$_2$ compounds.

1 Claim, No Drawings

11a-HOMO-PG INTERMEDIATES FOR PREPARING 11a-METHANO TXA₂ COMPOUNDS

CROSS REFERENCE TO RELATED APPLICATION

The present application is a division of Ser. No. 035,143, filed May 1, 1979 now U.S. Pat. No. 4,218,378.

BACKGROUND OF THE INVENTION

The present invention provides novel thromboxane analogs and intermediates. Particularly, the present invention provides novel 11a-homo-PG intermediates for preparing 11a-methano TXA₂ compounds. The essential material constituting a disclosure of the preparation and use of the compounds described above is incorporated here by reference from the U.S. Ser. No. 035,143 now U.S. Pat. No. 4,128,378.

PRIOR ART

Known in the art are the cyclohexane analogs of $PGF_{2\alpha}$ and $PGE_2$, e.g., 10a-homo-$PGF_{2\alpha}$ and 10a-homo-$PGE_2$. See Crossley, N. S., Tett. Lett. 36:3327–3330 (1971). Also racemic 11a-homo-$PGE_1$ is described by Floyd, M. B., et al., J. Org. Chem. 44:71–75 (1979). A related cyclohexene is describewd by Muchowski, J. M., et al., Prostaglandins 75:297–302 (1975) and certain 11-deoxy-11a-homo PG's are described in Derwent Farmdoc CPI 29086Y, abstracting French Pat. No. 2,327,768.

SUMMARY OF THE INVENTION

The present invention particularly provides a thromboxane intermediate of formula V, VI, VII, VIII, IX, or X,

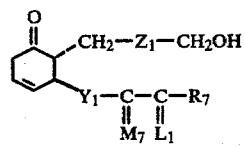   V

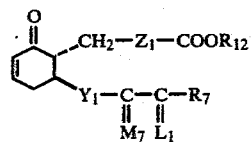   VIII

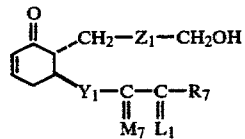   VI

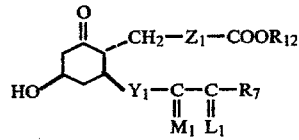   IX

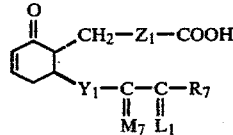   VII

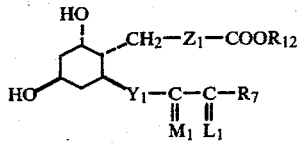   X wherein $M_7$ is $\alpha$-$R_5$:$\beta$-$OR_{10}$, $\alpha$-$OR_{10}$:$\beta$-$R_5$, or $\alpha$-H:$\beta$-H, wherein $R_{10}$ is a stable, acid hydrolyzable blocking group;

wherein $R_{12}$ is alkyl of one to 12 carbon atoms, inclusive, aralkyl of 7 to 12 carbon atoms, inclusive; phenyl; or phenyl substituted with one, two, or three chloro or alkyl of one to 3 carbon atoms;

wherein $Y_1$ is
(1) trans—CH=CH—,
(2) cis—CH=CH—,
(3) —CH₂CH₂—, or
(4) —C≡C—, wherein $M_1$ is $\alpha$-$R_5$:$\beta$-OH, $\alpha$-OH:$\beta$-$R_5$, or $\alpha$-H:$\beta$-H, wherein $R_5$ is hydrogen or methyl, and wherein $L_1$ is $\alpha$-$R_3$:$\beta$-$R_4$, $\alpha$-$R_4$:$\beta$-$R_3$, or a mixture of $\alpha$-$R_3$:$\beta$-$R_4$ and $\beta$-$R_3$:$\alpha$-$R_4$, wherein $R_3$ and $R_4$ are hydrogen, methyl, or fluoro, being the same or different, with the proviso that one of $R_3$ and $R_4$ is fluoro only when the other is hydrogen or fluoro, or wherein -C($M_1$)-C($L_1$)- is trans—CH=CH—;

wherein $Z_1$ is
(1) cis—CH=CH—CH₂—(CH₂)$_g$—CH₂—,
(2) cis—CH=CH—CH₂—(CH₂)$_g$—CF₂—, (3) cis—CH₂—CH=CH—(CH₂)$_g$—CH₂—,
(4) —(CH₂)₃—(CH₂)$_g$—CH₂—,
(5) —(CH₂)₃—(CH₂)$_g$—CF₂—,
(6) —CH₂—O—CH₂—(CH₂)$_g$—CH₂—,
(7) —(CH₂)₂—O—(CH₂)$_g$—CH₂—, or
(8) trans—CH₂—(CH₂)$_g$—CH₂-CH=CH-;
(9) —(m-Ph)—O—(CH₂)$_g$—, or
(10) —(m-Ph)—CH₂—(CH₂)$_g$—,
wherein g is one, 2, or 3 and -(m-Ph)- is meta-phenylene; and wherein $R_7$ is
(1) -(CH₂)$_m$-CH₃, wherein m is an integer from one to 5, inclusive;
(2) phenoxy;
(3) phenoxy substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl;
(4) phenyl;
(5) phenyl substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl;
(6) phenylmethyl, phenylethyl, or phenylpropyl; or
(7) phenylmethyl, phenylethyl, or phenylpropyl substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl; with the proviso that $R_7$ is phenoxy or substituted phenoxy, only when $R_3$ and $R_4$ are hydrogen or methyl, being the same or different.

DESCRIPTION OF THE PREFERRED EMBODIMENTS

The novel 11a-methano-TXA analogs of the present invention are all highly active as inhibitors of thromboxane synthetase and accordingly are useful for anti-inflammatory, anti-asthma, and anti-thrombotic indications.

I claim:

1. A thromboxane intermediate of formula V, VI, VII or VIII,

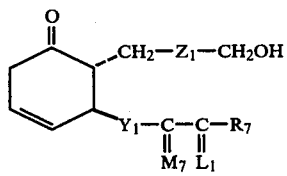

V

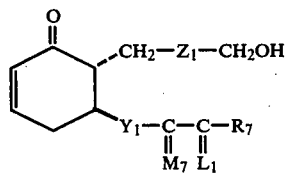

VI

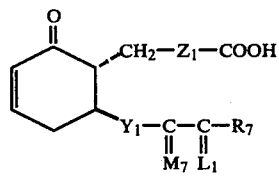

VII

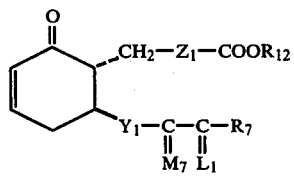

VIII wherein $M_7$ is $\alpha\text{-}R_5{:}\beta\text{-}OR_{10}$, $\alpha\text{-}OR_{10}{:}\beta R_5$, or $\alpha\text{-}H{:}\beta\text{-}H$, wherein $R_5$ is hydrogen or methyl and $R_{10}$ is a stable, acid hydrolyzable blocking group;

wherein $R_{12}$ is alkyl of one to 12 carbon atoms, inclusive, aralkyl of 7 to 12 carbon atoms, inclusive; phenyl; or phenyl substituted with one, two, or three chloro or alkyl of one to 3 carbon atoms;

wherein $Y_1$ is
(1) trans—CH=CH—,
(2) cis—CH=CH—,
(3) —CH$_2$CH$_2$—, or
(4) —C≡C—, wherein $L_1$ is $\alpha\text{-}R_3{:}\beta\text{-}R_4$, $\alpha\text{-}R_4{:}\beta\text{-}R_3$, or a mixture of $\alpha\text{-}R_3{:}\beta\text{-}R_4$ and $\beta\text{-}R_3{:}\alpha\text{-}R_4$, wherein $R_3$ and $R_4$ are hydrogen, methyl, or fluoro, being the same or different, with the proviso that one of $R_3$ and $R_4$ is fluoro only when the other is hydrogen or fluoro, wherein $Z_1$ is
(1) cis—CH=CH—CH$_2$—(CH$_2$)$_g$—CH$_2$—,
(2) cis—CH=CH—CH$_2$—(CH$_2$)$_g$—CF$_2$—,
(3) cis—CH$_2$—CH=CH—(CH$_2$)$_g$—CH$_2$—,
(4) —(CH$_2$)$_3$—(CH$_2$)$_g$—CH$_2$—,
(5) —(CH$_2$)$_3$—(CH$_2$)$_g$—CF$_2$—,
(6) —CH$_2$—O—CH$_2$—(CH$_2$)$_g$—CH$_2$—,
(7) —(CH$_2$)$_2$—O—(CH$_2$)$_g$—CH$_2$—, or
(8) trans—CH$_2$—(CH$_2$)$_g$—CH$_2$—CH=CH—;
(9) —(m-Ph)—O—(CH$_2$)$_g$—, or
(10) —(m-Ph)—CH$_2$—(CH$_2$)$_g$—, wherein g is one, 2, or 3 and -(m-Ph)- is meta-phenylene; and wherein $R_7$ is
(1) -(CH$_2$)$_m$-CH$_3$, wherein m is an integer from one to 5, inclusive;
(2) phenoxy;
(3) phenoxy substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl;
(4) phenyl;
(5) phenyl substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl;
(6) phenylmethyl, phenylethyl, or phenylpropyl; or
(7) phenylmethyl, phenylethyl, or phenylpropyl substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl; with the proviso that $R_7$ is phenoxy or substituted phenoxy, only when $R_3$ and $R_4$ are hydrogen or methyl, being the same or different.

* * * * *

UNITED STATES PATENT OFFICE
CERTIFICATE OF CORRECTION

Patent No. 4,259,250   Dated 31 March 1981

Inventor(s) Gordon L. Bundy

It is certified that error appears in the above-identified patent and that said Letters Patent are hereby corrected as shown below:

Column 1, line 18, "now U.S. Pat. No. 4,128,378" should read -- now U.S. Pat. No. 4,218,378 --.

Signed and Sealed this

Sixth Day of October 1981

[SEAL]

*Attest:*

*Attesting Officer*

GERALD J. MOSSINGHOFF

*Commissioner of Patents and Trademarks*